United States Patent
Cohen (10) Patent No.: US 7,815,949 B2
(45) Date of Patent: Oct. 19, 2010

(54) **ESTROGENIC EXTRACTS OF *MORUS ALBA* AND USES THEREOF**

(75) Inventor: Isaac Cohen, Piedmont, CA (US)

(73) Assignee: BioNovo, Inc., Emeryville, CA (US)

(*) Notice: Subject to any disclaimer, the term of this patent is extended or adjusted under 35 U.S.C. 154(b) by 473 days.

(21) Appl. No.: 11/298,080

(22) Filed: Dec. 9, 2005

(65) Prior Publication Data

US 2006/0134245 A1  Jun. 22, 2006

Related U.S. Application Data

(60) Provisional application No. 60/637,302, filed on Dec. 17, 2004.

(51) Int. Cl.
*A61K 36/00* (2006.01)
*A61K 9/00* (2006.01)
*A61K 47/00* (2006.01)

(52) U.S. Cl. ............... 424/774; 424/769; 424/725; 424/439; 424/400

(58) Field of Classification Search ............... None
See application file for complete search history.

(56) References Cited

U.S. PATENT DOCUMENTS

| | | | | |
|---|---|---|---|---|
| 5,164,182 A | * | 11/1992 | Meybeck et al. | ............. 424/773 |
| 5,674,497 A | * | 10/1997 | Kuwana et al. | ............. 424/765 |
| 6,280,715 B1 | | 8/2001 | Seguin et al. | |
| 6,348,204 B1 | | 2/2002 | Touzan | |
| 6,551,627 B1 | | 4/2003 | Yoon et al. | |

FOREIGN PATENT DOCUMENTS

| | | | |
|---|---|---|---|
| CN | 1105252 A | | 7/1995 |
| CN | 1176749 A | | 3/1998 |
| CN | 1321473 A | | 11/2001 |
| CN | 1471846 A | | 2/2004 |
| JP | 06183985 A | | 7/1994 |
| JP | 2001002568 | | 1/2001 |
| JP | 2002142717 A | | 5/2002 |
| JP | 2004 189609 A | | 7/2004 |
| WO | WO 2004/006946 | * | 1/2004 |

OTHER PUBLICATIONS

Supplemental EP Search Report mailed Apr. 14, 2008.
Ray et al., "Histological study on the effect of phytoestrogen on uterus and ovary of animal," 19660101, Indian Science Congress Association Proceedings 53(nr3):461, ISSN 0085-1817.
EP 05853308.4 Official Action mailed Jul. 13, 2010.

* cited by examiner

*Primary Examiner*—Christopher R Tate
*Assistant Examiner*—Randall Winston
(74) *Attorney, Agent, or Firm*—Wilson Sonsini Goodrich & Rosati (57) ABSTRACT

Extracts of various species of the Moraceae family have estrogenic properties. For example, aqueous and ethanolic extracts of *Morus alba* L. species possess estrogenic properties in both ERα+ and ERβ+ cells. These estrogenic effect include estrogen response element (ERE) stimulation as well as tumor necrosis factor (TNF) repression. Methods are provided for treating climacteric symptoms, breast and/or uterine cancer, and osteoporosis.

5 Claims, 1 Drawing Sheet

```
                             SEQUENCE LISTING

<160> NUMBER OF SEQ ID NOS: 1

<210> SEQ ID NO 1
<211> LENGTH: 19
<212> TYPE: DNA
<213> ORGANISM: Xenopus laevis

<400> SEQUENCE: 1
tcaggtcaca gtgacctga                                                  19
```

ESTROGENIC EXTRACTS OF *MORUS ALBA* AND USES THEREOF

CROSS-REFERENCE

This application claims the benefit of U.S. Provisional Application No. 60/637,302, filed Dec. 17, 2004, which is incorporated herein by reference in its entirety.

FIELD OF THE INVENTION

The present invention relates to plant extract compositions, and more particularly to compositions comprising extracts of plant species belonging to the species *Morus alba* L. (white mulberry). The invention further relates to methods of using and methods of making such plant extract compositions.

BACKGROUND OF THE INVENTION

Hormone replacement therapy (HRT) has been used successfully to treat a variety of conditions, such as osteoporosis, increased risk of cardiovascular disease in post-menopausal women and climacteric symptoms, such as hot flashes, decreased libido and depression. However, HRT with estradiol ($E_2$), either alone or in combination with progestin, can lead to undesirable effects. In fact, a recent Women's Health Initiative (WHI) study was abruptly halted when preliminary results showed that HRT was associated with a 35% increased risk of breast cancer.

Breast cancer can be treated or prevented by using a so-called selective estrogen receptor modulator (SERM), such as tamoxifen. (Before the approval of tamoxifen, breast cancer treatment of pre-menopausal women often included removing the ovaries in order to reduce the cancer-stimulating effect of estrogen.) Tamoxifen appears to selectively block the cancer-inducing effects of estrogen in breast tissues of pre-menopausal women. Another SERM, raloxifene, has been approved for treatment of osteoporosis as an alternative to estrogen replacement. In addition to selectively inducing estrogenic effects in bone tissue, long-term administration of raloxifene was also shown to be associated with reduction in the rate of breast cancer in the Multiple Outcomes of Raloxifene Evaluation (MORE) study.

While SERMs such as tamoxifen and raloxifene provide selective reduction in estrogen's cancer-inducing effects in the breast, they are not without their risks. For example both tamoxifen and raloxifene therapy have been associated with increased incidence of hot flushes; and tamoxifen therapy has been shown to increase the risk of uterine (endometrial) cancer.

Despite the success of estrogen replacement therapy in treating osteoporosis, coronary heart disease and climacteric symptoms, and despite the success of using SERMs like tamoxifen and raloxifene in treating breast cancer and osteoporosis, there remains a need for compositions having estrogenic properties. Additionally, given the increasing cost of producing drug compounds, there is a need for additional estrogenic compositions that may be obtained from natural sources.

Various cultivars of white mulberry (*Morus alba* L.) have been grown throughout the world for a wide variety of purposes. It generally grows as a tree or a shrub. In the Orient, it has been grown for centuries for its leaves, which are used as silk worm fodder, and secondarily as fodder for herbivorous livestock. In the United States, cultivation is believed to have been first attempted by Shakers, who intended to use the leaves as fodder for silk worms, however silk worm cultivation failed. White mulberry is now grown in the United States as an ornamental, as a wind break for edging fields, and for its fruit (although the fruit of black mulberry is preferred over that of white mulberry). In some parts of the southern United States, it is considered an invasive plant. It is readily adapted to growing in a number of soil types, elevations and latitudes. There is no known report of using extracts of *Morus alba* L. as estrogenic compositions.

There is a need for estrogenic compositions that are readily obtained from natural sources. There is also a need for methods of making such compositions. There is also a need for methods of using such estrogenic compositions.

SUMMARY OF THE INVENTION

The invention provides a plant extract composition that contains an extract of a plant species of the species *Morus alba* L.

The invention also provides a method of eliciting an estrogenic effect in a subject. The method includes administering to a subject an estrogenically effective amount of the estrogenic *Morus alba* L. extract composition.

The invention further provides a method of activating estrogen response element (ERE). The method includes contacting a cell, which has both a gene under control of an estrogen response element and an estrogen receptor, with an amount of the inventive *Morus alba* L. extract composition that is effective to activate the gene through interaction of the ER with the estrogen response element.

The invention further provides a method of repressing a gene under control of a tumor necrosis factor response element (TNF-RE). The method includes administering to a cell, which has a TNF response element (TNF-RE) operatively linked to a gene, an amount of the inventive *Morus alba* L. extract composition that is effective to repress expression of tumor necrosis factor. In some embodiments, the gene is TNF-α. In other embodiments, the gene is a reporter gene.

The invention further provides a method of making the inventive *Morus alba* L. extract composition. The method begins with obtaining plant matter from a plant of the species *Morus alba* L. The method continues with contacting the plant matter from a plant species of the species *Morus alba* L. with an extraction medium under conditions suitable to form an extract solution. The method then provides for separating the extract solution from the plant matter, and optionally reducing or diluting the extract solution, thereby forming the extract. When reduced, the extraction solution can be either a concentrate or a solid residue (residue). Whether reduced or not, the extraction solution, concentrate and residue are referred to collectively as an "extract".

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description, which sets forth illustrative embodiments, in which the principles of the invention are utilized, and the accompanying drawings of which:

DETAILED DESCRIPTION OF THE INVENTION

The invention provides a plant extract composition that contains an extract of the taxonomic species of plant referred to as *Morus alba* L. The invention also provides estrogenic methods of using the inventive compositions. Such estrogenic methods include in vivo methods and in vitro methods. The estrogenic compositions possess the ability to antagonize the activation of a gene under control of the estrogen response element (ERE) by estradiol ($E_2$) and an estrogen receptor (ER). Accordingly, suitable in vivo methods include treatment and/or prevention of medical indications that are responsive to antagonism of $E_2$-stimulated activation of gene expression. Suitable in vitro methods include use in methods of activating a gene under control of the estrogen response element (ERE) and methods of repressing expression of a gene under control of the tumor necrosis factor response element (TNF-RE). The invention further provides methods of making the inventive extracts.

Breast neoplasms are the most common cancers diagnosed in women. In 2000, 184,000 new cases of breast cancer were diagnosed and 45,000 women died from breast cancer. Although the cause of breast cancer is probably multifactorial, there is compelling clinical, epidemiological and biological research that indicate estrogens promote breast cancer: (a) Hormone replacement therapy (HRT) is associated with a 35% increased risk of breast cancer by a meta-analysis of 51 studies; (b) Breast cancer can be prevented with tamoxifen or raloxifene, which bind to ERs and antagonize the actions of estrogens in breast cells; (c) Bilateral oophorectomy in premenopausal women with breast cancer leads to increased survival; (d) Greater exposure to estrogens (early menarche or late menopause, relative risk=1.3 and 1.5 to 2.0, respectively) increases the incidence of breast cancer; (e) Estrogens increase the proliferation of ER positive breast cancer cells; and (f) Estrogens increase the production of growth promoting genes, such as cyclin DI, c-myc, and c-fos.

Approximately 60-70% of breast tumors contain estrogen receptors. For several decades, breast tumors have been analyzed for the presence of ERs. Approximately 70% of ER+ tumors are responsive to antiestrogen therapy. This observation has led to the notion that ER+ tumors have a better prognosis than ER negative tumors. However, the discovery of ERβ has complicated these interpretations and has raised some profound clinical questions. Understanding the role of ERα and ERβ is of paramount importance, because the current methods of determining whether tumors are ER+ uses an antibody that only detects ERα. Thus, most studies examining the effects ERs in breast tumors on clinical outcomes reflect the only ERα status. However, several recent studies have detected the presence of ERβ mRNA in human breast tumors. Most of the studies have relied on RT-PCR to measure ERβ, because of the lack of specific and sensitive antibodies to ERβ. Dotzlaw et al. were the first to detect ERβ in breast tumor biopsies by RT-PCR. They found 70% of the breast tumors expressed ERβ and 90% expressed ERα. Furthermore, they demonstrated that several ER negative cell lines also express ERβ mRNA. These findings suggest that ERβ is highly expressed in breast tumors, and that both ERα and ERβ are often coexpressed in many tumors. In fact, some ER− tumors contain ERβ. Dotzlaw et al. also showed that ERβ mRNA is significantly lower in ER+/PR− (PR being progestin receptor) tumors compared to ER+/PR+ tumors. The authors suggested that this observation indicates that ERβ expression is associated with a poorer prognosis, because ER+/PR+ are more likely to respond to tamoxifen. Other studies suggest that the presence of ERβ confers a poor prognosis. Speirs et al. found that most breast tumors express ERβ mRNA alone or in combination with ERα mRNA. Those tumors that express both ERα and ERβ mRNA were associated with positive lymph nodes and tended to be characterized as higher grade tumors. Furthermore, increased ERβ expression occurs in MCF-10F cells treated with chemical carcinogens, suggesting that the expression of ERβ may contribute to the initiation and progression of breast cancer. Recently, Jensen et al. analyzed the expression of ERβ in 29 invasive breast tumors by immunohistochemistry (IHC). They found that ERβ expression was associated with an elevation of specific markers of cell proliferation, Ki67 and cyclin A. Moreover, the highest expression of these proliferation markers was present in ERα+/ERβ+ tumors. Although the number of ERα−TERβ+ cases were very small (n=7) the authors suggested that ERβ mediates cell proliferation in breast tumors. Speirs et al. also reported ERβ mRNA is significantly elevated in the tamoxifen-resistant tumors compared to tamoxifen-sensitive tumors.

In contrast, other studies indicate that the presence of ERβ confers a favorable prognosis. Iwao et al. demonstrated that ERα mRNA is up-regulated and ERβ mRNA is down-regulated as breast tumors progress from preinvasive to invasive tumors. Using IHC of frozen tumor sections Jarvinen et al. found that ERβ expression was associated with negative axillary node status, low grade, and low S-phase fraction. A study by Omoto et al. also found that ERβ positive tumors correlated with a better prognosis than ERβ negative tumors, because the disease-free survival rate was higher in tumors containing ERβ. ERβ expression also showed a strong association with the presence of progesterone receptors and well-differentiated breast tumors. It has also been reported that the levels of ERβ are highest in normal mammary tissue and that it decreases as tumors progress from pre-cancerous to cancerous lesions. These studies indicate that ERβ may function as a tumor suppressor and that the loss of ERβ promotes breast carcinogenesis. In a study by Mann et al. it was shown that the expression of ERβ in more than 10% of cancer cells was associated with better survival in women treated with tamoxifen. The aggregate of these studies indicates the presence of ERβ confers a favorable prognosis. Consistent with RT-PCR and IHC data is a report that showed that adenovirus-mediated expression of ERβ resulted in a ligand-independent inhibition of proliferation of the ER negative cell line, MDA-MB-231.

These results demonstrate that the role of ERβ in the pathogenesis and prognosis of breast cancer is unclear. Several reasons may explain the apparent discrepancy among these studies. First, there may be a poor correlation between ERβ mRNA and ERβ protein. This notion is consistent with the presence of ERβ mRNA in some ER negative cell lines that do not have detectable ERs by ligand binding assays. Second, the IHC studies used different commercially available ERβ antibodies that have been poorly characterized for specificity and sensitivity. Third, most of the conclusions have been based on a few breast cancer cases. Clearly, more studies are needed to clarify the role of ERα and ERβ in breast cancer.

Role of SERMs as adjuvant therapy and chemoprevention in breast cancer: Because estrogens promote the proliferation of breast cancer cells, several therapeutic approaches have been implemented to block this effect of estrogens on breast tumors. These strategies, including ovarian ablation, antiestrogens, gonadotropin releasing hormone analogs or aromatase inhibitors, work by either decreasing the production of estrogens or blocking the action of estrogens. All of these strategies non-selectively block the action of both ERα and ERβ. The most common approach used clinically to prevent and treat breast tumors are the selective estrogen receptor modulators (SERMs), tamoxifen and raloxifene.

Tamoxifen is a non-steroidal triphenylethylene derivative that is the prototype SERM, because it exhibits antagonistic action in some tissues, such as the breast, but has agonist actions in other tissues such as the endometrium and bone. Tamoxifen has been extensively studied for its clinical effectiveness as an adjuvant therapy to reduce the recurrences of breast tumors in women with estrogen receptor-positive breast cancer. Five years of tamoxifen therapy reduces the risk of recurrences by 42%, mortality from breast cancer by 22% and a second contralateral primary breast tumor. Approximately, ⅔ of ER positive breast tumors respond to tamoxifen, whereas very little evidence indicates that women with ER negative tumors benefit from adjuvant tamoxifen. Most recently, the U.S. Breast Cancer Prevention Trial (BCPT) demonstrated that tamoxifen reduces the risk of primary invasive breast cancer by 49% in women considered to be at high risk for breast cancer. These studies demonstrate that tamoxifen is a first-line effective adjuvant therapy in women with a history of breast cancer and is an effective chemoprevention agent for women who are high risk for developing breast cancer.

Raloxifene is a member of the benzothiophene class of SERMs that has recently been approved for the prevention and treatment of osteoporosis. Raloxifene has not been evaluated for effectiveness as an adjuvant therapy for women with breast cancer. However, the Multiple Outcomes of Raloxifene (MORE) trial evaluated the effect of raloxifene on preventing breast cancer. The MORE trial was a randomized, placebo-controlled three-year study of 7705 postmenopausal women who have osteoporosis. In the MORE trial, 13 cases of breast cancer were found among the 5129 women in the raloxifene treatment group, versus 27 among the 2576 women who received placebo (RR=0.24), after a median follow-up of 40 months. Like tamoxifen, raloxifene is effective at reducing the incidence of estrogen receptor positive tumors, but not estrogen receptor negative tumors. Additional evidence for a role of estrogens in promoting breast cancer comes from a recent study that showed raloxifene only prevents breast cancer in postmenopausal women who have detectable levels of serum estradiol.

Structure of Estrogens Receptors: The fact that SERMs only work on ER positive tumors indicates that they need to interact with estrogen receptors in order to exert their protective effects on the breast. There are two known estrogen receptors, ERα and ERβ which are members of the steroid nuclear receptor super family. ERα was first cloned in 1986, and surprisingly about 10 years later a second ER was discovered, termed ERβ. ERα contains 595 amino acids, whereas ERβ contains 530 amino acids. Both receptors are modular proteins made up of three distinct domains. The amino-terminus domain (A/B domain) is the least conserved region, exhibiting only a 15% homology between ERα and ERβ. This domain harbors an activation function (AF-1) that can activate gene transcription activation in the absence of estradiol. The central region of ERs contains two zinc finger motifs that bind to an inverted palindromic repeat sequence separated by three nucleotides located in the promoter of target genes. The DNA binding domains (DBD) in ERα and ERβ are virtually identical, exhibiting 95% homology.

The carboxy-terminus domain contains the ligand binding domain (LBD), which carries out several essential functions. The LBD contains a region that forms a large hydrophobic pocket where estrogenic compounds bind, as well as regions involved in ER dimerization. The LBD also contains a second activation function (AF-2) that interacts with coregulatory proteins. AF-2 is required for both estrogen activation and repression of gene transcription. The LBDs of ERα and ERβ are only about 55% homologous. The striking differences in the amino acid composition of the ERα and ERβ LBDs may have evolved to create ERs that have distinct transcriptional roles. This would permit ERα and ERβ to regulate the activity of different genes and to elicit different physiological effects. This notion is supported by studies of ERα and ERβ knockout mice. For example, the ERα knockout mice have primitive mammary and uterine development, whereas the ERβ knockout mice develop normal mammary glands and uterus. These observations demonstrate that only ERα is required for the development of these tissues. Furthermore, ERα is more effective than ERβ at activating genes, whereas ERβ is more effective than ERα at repressing gene transcription.

Mechanisms of action of estrogens: Estrogens can activate or repress gene transcription. There are two characterized pathways for activation of gene transcription, the classical ERE (estrogen response element) pathway and the AP-1 pathway. There are at least three essential components necessary for estrogens to regulate the transcription of genes: the ERs (ERα and/or ERβ), the promoter element in target genes and coregulatory proteins. The binding of estradiol to the ER leads to a conformational change, which results in several key steps that initiate transcriptional pathways. First, the interaction of $E_2$ with ER leads to the dissociation of chaperone proteins; this exposes the ER's dimerization surface and DNA binding domain. Loss of the chaperone proteins allows the ERs to dimerize and bind to an ERE in the promoter region of a target gene.

Second, the binding of $E_2$ moves helix 12 of the Ek's LED to create a surface that assembles the AF-2 function of the ER. The AF-2 consists of a conserved hydrophobic pocket comprised of helices 3, 5 and 12 of the ER, which together form a binding surface for the p160 class of coactivator proteins (coactivators), such as steroid receptor coactivator-1 (SRC-1) or glucocorticoid receptor interacting protein 1 (GRIP 1). Coactivators (also known as "coregulators") contain several repeat amino acid motifs comprised of LXXLL, which project into hydrophobic cleft surrounded by the AF-2's helices. The coactivators possess histone acetylase activity. It is thought that gene activation occurs after the ERs and coactivator proteins form a complex on the ERE that causes the acetylation of histone proteins bound to DNA. The acetylation of histones changes the chromatin structure so that the ER/coregulator complex can form a bridge between the ERE and basal transcriptional proteins that are assembled at the TATA box region of the target gene to initiate gene transcription.

Effect of SERMs on the ERE pathway: Unlike estrogens, SERMs do not activate the ERE pathway. Instead, the SERMs competitively block the effects of estrogens on the ERE pathway. Like estrogens, SERMs bind to ERα and ERβ with high affinity and cause the dissociation of chaperone proteins, ER dimerization and binding of ERs to the ERE. Thus, the antagonist action of SERMs occurs at a step distal to the binding of the ER to the promoter region. The molecular mechanism of the antagonist action of the SERMs has been clarified by the crystallization of the ERα and ERβ LBDs. It is clear from the structure of the ER LBDs that $E_2$, tamoxifen and raloxifene bind to the same binding pocket. However, tamoxifen and raloxifene contain a bulky side-chain that is absent in $E_2$. The ER x-ray structures have revealed that the bulky side chain of SERMs obstructs the movement of the LBD, which prevents the formation of a functional AF-2 surface. Remarkably, when a SERM binds to ERα a sequence (LXXML) in helix 12, which is similar to the LXXLL motif, interacts with the hydrophobic cleft of the AF-2 surface to occlude the coactivator recognition site. Thus, unlike estrogens, SERMs do not create a functional AF-2 surface; this prevents the binding of coactivators. Because the coactivator proteins do not bind to the AF-2 surface in the presence of SERMs, the activation pathway is abruptly halted. Instead of recruiting coactivator, ERs liganded with SERMs recruit corepressors, such as N-CoR.

These studies demonstrated that the antagonist properties of SERMs are due to at least three factors. First, SERMs bind to the same binding pocket as estrogens and competitively block their binding to the ERs. Second, SERMs prevent ER from interacting with coactivator proteins that are required for transcriptional activation of the ERE pathway. Third, SERMs recruit corepressors, which prevent transcriptional activation of genes. These actions of SERMs most likely explain how raloxifene and tamoxifen act as antagonists in breast cells to inhibit development of breast cancer.

SERMs are also more effective than $E_2$ at activating genes with an AP-1 element. In fact, $E_2$ is an antagonist of SERM-mediated activation of AP-1 elements. It has been postulated that SERMs exhibit agonistic actions in tissues, such as the bone and endometrium by activating the AP-1 pathway. Interestingly, SERMs are more potent at activating the AP-1 pathway in the presence of ERβ, which indicates that SERMs will trigger the AP-1 pathway more efficiently in tissues that are rich in ERβ. The role of the AP-1 pathway in estrogen-mediated breast carcinogenesis is unclear, because estrogens are much weaker at activating the AP-1 pathway compared to SERMs. However, it has been proposed that the AP-1 pathway may be involved in resistance to tamoxifen in breast tumors.

In accordance with aspects of the present invention, studies have been performed, which demonstrate that: ERβ is weaker than ERα at activating ERE-tk-Luc; ERβ is more effective than ERα at repressing the TNF-RE-tk-Luc; and that ERβ inhibits ERα-mediated transcriptional activation of ERE-tk-Luc. Detailed experiments are discussed in the Examples section hereinafter.

The invention provides a plant extract composition that contains an extract of the taxonomic species Morus alba L. An "extract" is a composition of matter prepared by contacting an extraction medium (solvent) with plant matter under conditions suitable for drawing one or more chemical compounds from the plant matter into the extraction medium, forming an extraction solution. The extraction solution is then separated from the plant matter, and is optionally diluted or reduced, to form the extract.

The extract of the invention comprises phytochemicals obtained from plant matter the plant species Morus alba L. Plant matter is further defined hereinafter.

The species Morus alba L. is also variously referred to as white mulberry, Russian mulberry, silkworm mulberry. It is grown as a tree or shrub throughout the world, generally in temperate to tropical climes. Various cultivars are available, and may generally be obtained from commercial sources, such as nurseries.

The extraction medium is a suitable liquid solvent, e.g. water or ethanol. The extraction medium is in some cases water, ethanol or another relatively polar liquid solvent. In some cases, the extraction medium is either diluted or reduced. The extraction medium may be fully reduced, whereby the extract takes the form of a residue (residual extract). Thus, the extract contains at a minimum one or more plant-derived compounds (phytochemicals), optionally dissolved in a solvent. A reduced or residual extract may be reconstituted by adding a suitable diluent, e.g. water and/or ethanol, to form a reconstituted extract.

Inventive compositions comprising plant extracts include neat extracts (aqueous or ethanol, concentrates, residues) and combinations of such extracts with one or more additional ingredients. Inventive compositions include those in a variety of physical forms, including solid, semi-solid, liquid, colloidal, etc. Where the compositions according to the invention are intended for pharmaceutical use, the additional ingredients are pharmaceutically acceptable. Where the compositions according to the invention are intended for use in assays or other uses that are not directed toward a living body, the additional ingredient(s) may be either pharmaceutically acceptable or not.

Suitable additional ingredients include solvents. Solvents may be subdivided into pharmaceutically acceptable and non-pharmaceutically acceptable solvents. In this context, it is to be understood that some pharmaceutically acceptable solvents include water for injection (WFI), which may be pH adjusted and/or buffered to a pre-selected pH or pH range, e.g. from about 2 to about 8, more specifically from about 4.0 to about 7.5, and more particularly from about 4.9 to about 7.2.

Pharmaceutically acceptable solvents may further comprise one or more pharmaceutically acceptable acids, bases, salts or other compounds, such as carriers, excipients, etc. Pharmaceutically acceptable acids include HCl, $H_2SO_4$ $H_3PO_4$, benzoic acid, etc. Pharmaceutically acceptable bases include NaOH, KOH, $NaHCO_3$, etc. Pharmaceutically acceptable salts include NaCl, NaBr, KCl, etc. Acids and bases may be added in appropriate proportions to buffer a pharmaceutically acceptable solution at a particular, pre-selected pH, especially a pH in the range of about 2-8, more especially in the range of about 5.0 to about 7.2

An extract of the invention may be administered orally, intravenously, subcutaneously, intraperitoneally, intranasally, by inhalation or by direct gastric administration, e.g. through a naso-gastral (NG) tube. The amount of extract administered varies with patient weight, age, physical condition and therapeutic endpoint sought. The amount of administered extract may conveniently be expressed as the dry mass of the solid residue when the extract is lyophilized or evaporated to dryness. The equivalent dry mass of a therapeutic solution comprising the extract of the invention is thus the amount of dry extract contained within the therapeutic solution. The equivalent dry mass can be measured by measures known in the art, such as by UV/V is spectroscopy. This method entails preparing a standard curve with known concentrations of dry extract in known quantities of diluent and preparing a standard curve of concentration versus optical density (O.D.). Once the standard curve has been prepared, the concentration of dry extract in a therapeutic solution can then be measured by obtaining the O.D. of the solution and correlating this value to the corresponding concentration on the standard curve. In general, a therapeutic composition according to the invention comprises from about 0.001 µg/mL to about 1 mg/mL of dry extract. A therapeutic daily dose of the extract of the invention varies with indication, age and body weight of the patient, and is in general in the range of about 0.1 µg to 100 mg per Kg body weight of the patient.

Plant extracts according to the present invention provide estrogenic activation of genes under control of the estrogen response element (ERE). Accordingly, in some cells an inventive plant extract possesses estrogenic properties—i.e. contacting a cell comprising an ERE and an ER (ERα, ERβ or both) with an inventive plant extract gives rise to stimulation of a gene under control of the ERE. In an in vitro cell system, ERE-mediated activation by an inventive estrogenic plant extract leads to expression of a gene that is operatively linked to the ERE. In particular embodiments, estrogenic interaction of an ER with an ERE linked to the minimal thymidine kinase promoter and the luciferase gene gives rise to enhanced luciferase expression. Thus, the plant extracts of the present invention may be used to identify ERα+ cell lines, ERβ+ cell lines and/or ERα+/ERβ+ cell lines having an ERE-containing promoter operatively linked to a reporter gene, such as luciferase. Plant extracts of the present invention may also be used as assay reagents, including standards, for identifying compounds having estrogenic effects in ER+ cell lines.

In one such assay method, an inventive plant extract is first prepared at a known activity or concentration. Quantification of the inventive plant extract is conveniently carried out by taring a container, measuring into the container a known volume of the plant extract, reducing the plant extract by evaporation or lyophilization to produce a residue, and obtaining the mass of the container plus plant extract. The difference in mass between the container plus plant extract and the tare mass is the dry mass of the plant extract. The ratio of dry mass of plant extract per volume of plant extract is the concentration per unit volume. The plant extract may be used in its initial form, using the results of the foregoing quantitation method to specify its concentration. The residue can also be reconstituted by addition of water or another suitable solvent system to form a plant extract solution of known concentration.

Once the concentration of plant extract is known, a standard curve is prepared. In general the ER+ cells are contacted with the plant extract and a signal relating to estrogenic activity is recorded. In particular, an ER+ cell has a reporter gene under the control of an ERE. This ER+ cell is contacted with a plant extract of the invention, which gives rise to a reporter signal in proportion to the amount of plant extract added. This step may be carried out with multiple samples at the same plant extract concentration, at different plant extract concentrations, or both. As an example, nine samples may be tested: the first three at a first concentration, the next three at a concentration that is a half log greater than the first, and the next three at a concentration a whole log greater than first. The reporter signals are then observed and recorded, and the resulting data points (plant extract concentration versus reporter signal strength) are fitted to a standard curve by a conventional curve-fitting method (e.g. least squares).

To evaluate the estrogenic effect of a candidate compound, a candidate compound is contacted with E+ cells having the reporter gene under control of the ERE. The reporter gene signal is observed and compared to the standard curve to quantitate the candidate compound's relative estrogenic effect.

The ER+ cell line used in the foregoing method may be a cell line that naturally expresses ER, e.g. a human-derived ER+ breast cell carcinoma cell line. In some embodiments, the ER+ tissue is an immortalized human cell line, e.g. an immortalized bone marrow or breast cell line. Exemplary cell lines include human monocyte, osteoblast, malignant breast carcinoma and immortalized epithelil breast cell lines. Particular cell lines that may be mentioned include U937, U2OS, MDA-MB-435 and MCF-7 cell lines. Other ER+ cell lines, including immortalized cell lines, may also be used. Alternatively, the ER+ cell line may be a cell line that does not naturally express ER, such as a bacterial cell line, that has been transformed with an ER expression vector.

The ER+ cell line is transformed with a vector having a promoter containing an ERE that controls a reporter gene. For example, the vector may be a viral vector containing ERE, a minimal thymidine kinase promoter (tk) and a luciferase gene (Luc). The construct is transfected into the target cell by known methods and expression of the ERE-tk-Luk system is confirmed by e.g. performing the foregoing assay on putative ER+ cells in the presence of known quantities of $E_2$. Other methods of verifying successful transformation of ER+ cells include immunostaining with known ER antibodies.

The ERE-containing promoter is a DNA containing an ERE sequence and a promoter sequence. The promoter sequence is an art-recognized promoter sequence, such as the minimal thymidine kinase (tk) promoter sequence. Other ERE-containing promoters are possible and are within the scope of the instant invention. The ERE and promoter sequence operate together to control expression of the reporter gene. As described herein, the estrogenic compound (plant extract or $E_2$, for example) binds to the ER, giving rise to ER dimer and forming the AF-2 surface. The ER dimer then binds to the ERE, activating the gene under control of the promoter. In some embodiments, the ERE is directly upstream of (5'- to) the promoter, to which it is directly ligated.

The reporter gene is a gene which, when expressed, gives rise to a detectable signal. The luciferase gene is a suitable reporter gene because it gives rise to the protein luciferase, which generates a detectable light signal in the presence of a single reagent, luciferin. In particular, the cDNA of the luciferase gene is expressed to produce the 62 kDa enzymatic protein, luciferase. The luciferase enzyme catalyzes the reaction of luciferin and ATP in the presence of $Mg^{2+}$ and oxygen to form oxyluciferin, AMP, pyrophosphate (PPi) and emitted light. The emitted light is yellow-green (560 nm), and may easily be detected using a standard photometer. Because ATP, $O_2$ and $Mg^{2+}$ are already present in cells, this reporter gene only requires addition of the reagent luciferin to produce a detectable signal, and is especially well-suited for use in assays of the present invention. Other reporter genes that may be mentioned as being available in the art include chloramphenicol transacetylase (CAT), neomycin phosphotransferase (neo) and beta-glucuronidase (GUS).

In some assay methods of the invention, it is useful to further characterize the standard plant extract by comparison with one or more estrogenic compounds, SERMs, etc. Such assay methods are performed essentially as described above, making the proper substitutions of standard estrogenic compound and/or SERMs for plant extract in the appropriate parts of the method.

Plant extracts according to the present invention also repress gene expression by the TNF-RE-mediated pathway. In some cases, plant extracts of the invention repress gene expression in vitro, especially in cells having a reporter gene (e.g. the luciferase gene, Luc) under control of a TNF-RE. In some cases, plant extracts of the invention repress expression of TNF-α, which is a cytokine produced primarily by monocytes and macrophages. This cytokine is found in synovial cells and macrophages in various tissues, and has been strongly implicated in rheumatoid arthritis (RA). TNF-α is also expressed in other inflammatory diseases, and also as a response to endotoxins from bacteria. As repressors of TNF expression via the TNF-RE repressor pathway, plant extracts of the invention are of interest in the treatment of inflammatory disorders associated with elevated levels of TNF.

In some embodiments of the invention, a cell line is prepared, which expresses one or both of ERα and ERβ as well as a reporter gene under control of TNF-RE. The TNF-RE is generally upstream of (5'- to) the reporter gene, and signal detection is carried out as previously described herein.

The foregoing cell TNF-RE-containing cell system further contains one or more copies of an ER gene—i.e. ERα, ERβ or both. The ER+ cell line used in the foregoing method may be a cell line that naturally expresses ER, e.g. a human-derived ER+ breast cell carcinoma cell line. In some embodiments, the ER+ tissue is an immortalized human cell line, e.g. an immortalized bone marrow or breast cell line. Exemplary cell lines include human monocyte, osteoblast, malignant breast carcinoma and immortalized epithelial breast cell lines. Particular cell lines that may be mentioned include U937, U2OS, MDA-MB-435 and MCF-7 cell lines. Other ER+ cell lines, including immortalized cell lines, may also be used. Alternatively, the ER+ cell line may be a cell line that does not naturally express ER, such as a bacterial cell line, that has been transformed with an ER expression vector.

In the presence of a predetermined amount of luciferin, and in the absence of an estrogenic compound, e.g. $E_2$ or a plant extract of the invention, the cell system emits a yellow light (560 nm) at an intensity, called the "control intensity" or the "baseline intensity". Light emission at 560 nm is conveniently quantified in optical density units ($O.D._{560nm}$). Upon addition of an estrogenic compound, e.g. $E_2$ or one of the inventive plant extracts, the intensity of 560 nm light emissions is attenuated as compared to the control. Remarkably, in the presence of a SERM, such as tamoxifen or raloxifene, luciferase expression increases and 560 nm light emission intensity also increases. Thus, plant extracts of the invention are capable of inducing an estrogenic TNF-RE-controlled repression of gene expression.

The TNF-RE-containing cell system can be used in an assay method according to the invention. In the inventive assay methods, the attenuation of luciferase activity (i.e. decreased emission of 560 nm light), correlates with increased estrogenic activity, whereas activation of luciferase activity (i.e. increased emission at 560 nm), correlates with anti-estrogenic activity. Standard curves may be prepared using known quantities of the inventive plant extracts, as described herein. Such standard curves may be further augmented by using other known estrogenic or anti-estrogenic standards, such as $E_2$ or some other known estrogenic compound, and/or an anti-estrogenic SERM such as tamoxifen or raloxifene.

Cells from the transformed E+ cell line are then exposed to a candidate compound, the luciferase signal observed, and the signal compared to the previously prepared standard curve(s), as described herein. A compound that causes an increase of luciferase activity as compared to control (baseline), will be characterized as an anti-estrogenic SERM, whereas a compound that causes a decrease in luciferase activity versus control will be classified as estrogenic. The estrogenic or anti-estrogenic effect can then be quantified by comparing the degree of luciferase expression decrease or increase against the decrease brought about by the inventive plant extract, and optionally the respective signal decrease or increase brought about by $E_2$, tamoxifen and/or raloxifene.

Plant extract compositions of the present invention also antagonize the interaction of $E_2$-ER with ERE. In particular, it has been shown in that extracts of *Morus alba* L. antagonize the activation of ERE-tk-Luc by $E_2$ by directly interacting with ERβ and ERα. As antagonists of $E_2$-ER activation of ERE-controlled genes, the inventive plant extract compositions are considered to be similar in effect to tamoxifen, possessing prophylactic, palliative and/or anti-proliferative activity against breast cancer and uterine cancer.

The invention provides in vivo estrogenic methods of using the inventive compositions. In general, in vivo methods comprise administering to a subject an amount of the plant extract sufficient to bring about an estrogenic effect in the subject. The in vivo methods will give rise to estrogenic ERE-controlled gene activation, TNF-RE-controlled gene repression (e.g. TNF-α repression), or both. Thus, the in vivo methods will give rise to varied positive phenotypic effects in vivo.

The subject may be a mammal, such as a mouse, rat, rabbit, monkey, chimpanzee, dog, cat or a sheep, and is generally female. The subject may also be human, especially a human female. In some embodiments, the subject is a post-menopausal or post-oophorectomic female, and is in need of estrogenic therapy. In such case, the subject may be suffering from climacteric symptoms, such as hot flashes, insomnia, vaginal dryness, decreased libido, urinary incontinence and depression. In other such cases, the subject may be susceptible to, or suffering from, osteoporosis. Suitable in vivo methods include treatment and/or prevention of medical indications that are responsive to estrogen replacement therapy.

Administration of the compositions according to the present invention will be via a commonly used administrative route so long as one or more of the plant extracts is available to target tissue via that route. Some administrative routes that may be mentioned include: oral, nasal, buccal, rectal, vaginal and/or topical (dermal). Alternatively, administration may be by orthotopic, intradermal, subcutaneous, intramuscular, intraperitoneal or intravenous injection. Such compositions would normally be administered as pharmaceutically acceptable compositions, described supra.

Treatment (and its grammatical variants—e.g. treat, to treat, treating, treated, etc.) of a disease, disorder, syndrome, condition or symptom includes those steps that a clinician would take to identify a subject to receive such treatment and to administer a composition of the invention to the subject. Treatment thus includes diagnosis of a disease, syndrome, condition or symptom that is likely to be ameliorated, palliated, improved, eliminated, cured by administering the estrogenic plant extract of the invention to the subject. Treatment also includes the concomitant amelioration, palliation, improvement, elimination, or cure of the disease, disorder, syndrome, condition or symptom. In some embodiments, treatment implies prevention or delay of onset of a disease, disorder, syndrome, condition or symptom m (i.e. prophylaxis), prevention or delay of progression of a disease, disorder, syndrome, condition or symptom, and/or reduction in severity of a disease, disorder, syndrome, condition or symptom. In the case of neoplastic growth in particular, treatment includes palliation, as well as the reversal, halting or delaying of neoplastic growth. In this regard, treatment also includes remission, including complete and partial remission. In the case of climacteric symptoms, treatment includes prevention and palliation of various symptoms.

Prevention (and its grammatical variants) of a disease, disorder, syndrome, condition or symptom includes identifying a subject at risk to develop the disease, disorder, syndrome, condition or symptom, and administering to that subject an amount of the inventive plant extract sufficient to be likely to obviate or delay the onset of said disease, disorder, syndrome, condition or symptom. In some cases, prevention includes identifying a post-menopausal woman who the clinician believes, applying a competent standard of medical care, to be in need of hormone replacement therapy, and administering a plant extract of the present invention to the woman, whereby one or more climacteric symptoms is blocked or delayed. In some embodiments, prevention of osteoporosis includes identifying a post-menopausal woman who the clinician believes, applying a competent standard of medical care, to be at risk for developing osteoporosis, and administering a plant extract of the present invention to the woman, whereby the onset of bone loss is blocked or delayed.

Palliation includes reduction in the severity, number and/or frequency of occurrences of an a disease, disorder, syndrome, condition or symptom. Palliation of climacteric symptoms includes reducing the frequency and/or severity of hot flashes, insomnia, incontinence, depression, etc.

Treatment of osteoporosis includes identifying a person, such as a post-menopausal woman, at risk for bone loss, and administering a plant extract of the present invention to the woman, whereby bone loss is reduced in severity, delayed in onset, or prevented. In some embodiments, treatment of osteoporosis can also include addition of bone mass.

The invention further provides methods of making the inventive extracts of Morus alba L. The invention specifically provides a method of making an inventive estrogenic plant extract. The method includes obtaining a quantity of plant matter from a plant of the species Morus alba L., optionally comminuting the plant matter, contacting said plant matter with an extraction medium, and separating the plant matter from the extraction medium.

In some embodiments, the plant species are of the plant species Morus alba L. are various cultivars of Morus alba L.

Plant matter means any part or parts of at least one plant from the species Morus alba L. Plant matter includes the whole plant or any part or parts of the plant, such as the root, bark, wood, leaves, flowers (or flower such as: sepals, petals, stamens, pistils, etc.), fruit, seeds and/or parts or mixtures of any of the foregoing. Plant matter may be fresh cut, dried (including freeze dried), frozen, etc. Plant matter may also be whole or separated into smaller parts. For example, leaves may be chopped, shredded or ground; roots may be chopped or ground; fruit may be chopped, sliced or blended; seeds may be chopped or ground; stems may be shredded, chopped or ground. In particular embodiments of the invention, the plant parts used are the leaves of Morus alba L.

Plant extract compositions of the invention contain at least one extract of an Morus alba L. An "extract" is a solution, concentrate or residue that results when a plant part is contacted with an extraction solvent under conditions suitable for one or more compounds from the plant to partition from the plant matter into the extraction solvent; the solution is then optionally reduced to form a concentrate or a residue.

Suitable extraction media for the present invention include water and ethyl alcohol. Specifically, where water is the extraction solvent, purified water is suitable. Purified water includes distilled water, deionized water, water for injection, ultrafiltered water, and other forms purified of water. Ethyl alcohol that is employed in some embodiments of the invention is grain ethanol, and in particular undenatured ethanol (e.g. pure grain ethanol, optionally containing some water, e.g. up to about 10% water). In some embodiments, the extraction solvent is water, ethanol, or a mixture thereof. A concentrate or residue may be prepared by reducing (e.g. evaporating or lyophilizing) the extraction solution. Whether in the original extraction solvent, reduced concentrate, or residue form, each of these preparations is considered an "extract" for the purposes of the invention.

A method of producing the plant extract according to the invention optionally comprises first comminuting the plant matter in order to increase its surface area to volume ratio and to concomitantly increase efficiency of the extraction process. Methods of comminuting plant matter include grinding, chopping, blending, shredding, pulverizing, triturating, etc.

The extraction medium (solvent) is then contacted with the plant matter under conditions suitable for causing one or more phytochemicals, in particular estrogenic phytochemicals, to partition from the plant matter into the extraction medium. Such conditions include, in some cases, heating the extraction medium to a temperature above room temperature, agitation, contact time, etc. Exemplary temperatures for extraction are from about 50° C. to the boiling point of the extraction solvent. Where water is the extraction solvent, the extraction temperature is generally from room temperature to about 100° C.; temperatures of from about 50° C. to about 80° C. are especially suitable, and temperatures of about 75° C. are particularly suitable. In the case of ethanol as an extraction solvent, the extraction temperature is generally from about room temperature to about 78.5° C.; temperatures of from about 50° C. to about 78° C. are especially suitable and a temperature of about 75° C. is particularly suitable. The person of skill in the art will recognize that the proper balance should be drawn between extraction efficiency on the one hand and phytochemical compound stability on the other.

Once the extraction medium and the plant matter are combined, they are optionally agitated to ensure efficient exchange of estrogenic compound from the plant matter into the extraction medium, and are left in contact for a time sufficient to extract a useful amount of phytochemical compound from the plant matter into the extraction medium. After such time has elapsed (e.g. from about 5 min. to about 10 hr., more particularly from about 10 min. to about 5 hr., especially about 30 min. to about 2 hr.), the extraction medium containing the phytochemical compounds is separated from the plant matter. Such separation is accomplished by an art-recognized method, e.g. by filtration, decanting, etc.

A composition according to the invention includes an inventive plant extract or a composition comprising an inventive plant extract of the invention. In such embodiments, the inventive composition will optionally contain one or more additional ingredients. Such additional ingredients may be inert or active. Inert ingredients include solvents, excipients and other carriers. Active ingredients include active pharmaceutical ingredients (APIs), including those that exhibit synergistic activity in combination with the inventive plant extract.

EXAMPLES

The invention may be more fully appreciated with reference to the following illustrative and non-limiting examples.

Example 1

ERβ is weaker than ERα at activating ERE-tk-Luc: The effects of $E_2$ on transcriptional activation were examined by transfecting a plasmid containing a classical ERE upstream of the minimal thymidine kinase (tk) promoter linked to the luciferase reporter cDNA and an expression vector for ERα or ERβ. $E_2$ produced a 10-fold greater activation of the ERE in the presence of ERα compared to ERβ in human monocytic U937 cells, but the EC50 values were similar.

Example 2

ERβ is more effective than ERα at repressing the TNF-RE-tk-Luc: The effects of effects of $E_2$ on ERα and ERβ-mediated transcriptional repression were then compared using the −125 to −82 region of the TNF-α promoter, known as the tumor necrosis factor-response element (TNF-RE). TNF-α produced a 5-10-fold activation of 3 copies of the TNF-RE (−125 to −82) upstream of the tk promoter (TNF-RE-tk-Luc). $E_2$ repressed TNF-α activation of TNF-RE-tk-Luc by 60-80% in the presence of ERα and ERβ3. However, ERβ was approximately 20 times more effective than ERα at repression ($IC_{50}$ of 241 pM for ERα versus 15 pM for and ERβ, respectively). It was also found that ERβ is more effective than ERα at repressing the native −1044 to +93 TNF-α promoter. Thus, ERα is much more effective than ERβ at transcriptional activation, whereas ERβ is more effective than ERα at transcriptional repression. In contrast to $E_2$, the antiestrogens, tamoxifen, raloxifene and ICI 182,780 produced a 2-fold activation of TNF-RE-tk-Luc. Furthermore, these antiestrogens abolished the repression induced by $E_2$.

Example 3

Figure 1:
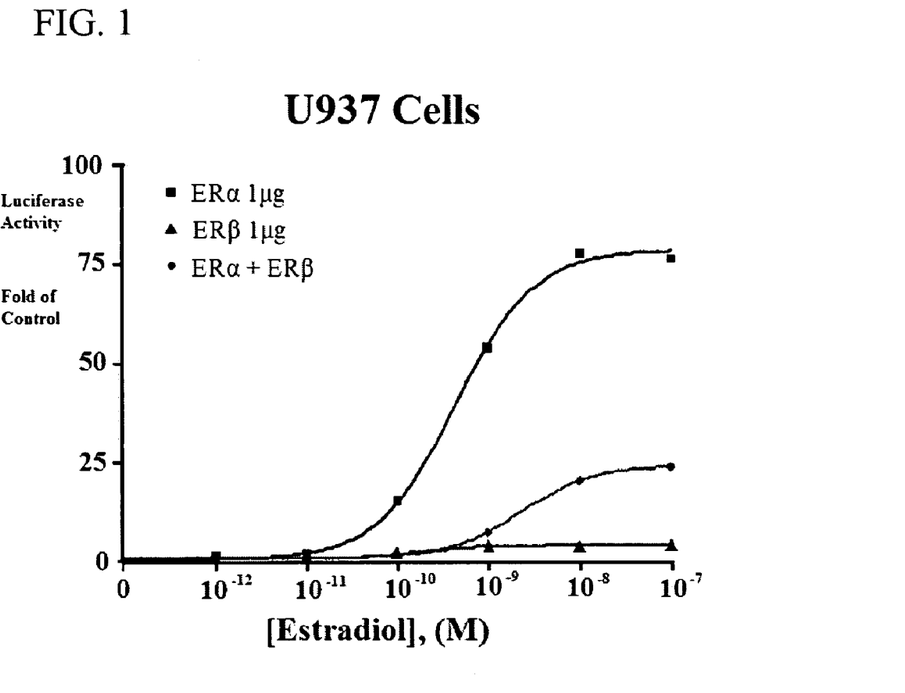
FIG. 1 is a graph of luciferase expression in U937 (human monocyte) cells transformed with DNA encoding estrogen response element linked to the minimal thymidine kinase (tk) promoter and a sequence encoding luciferase (Luc) in response to varying concentrations of estradiol ($E_2$) in the presence of either estrogen receptor alpha (ERα), estrogen receptor beta (ERβ) or both. ERβ has much less stimulatory effect on the ERE than does ERα in the presence of $E_2$.
Figure 2:
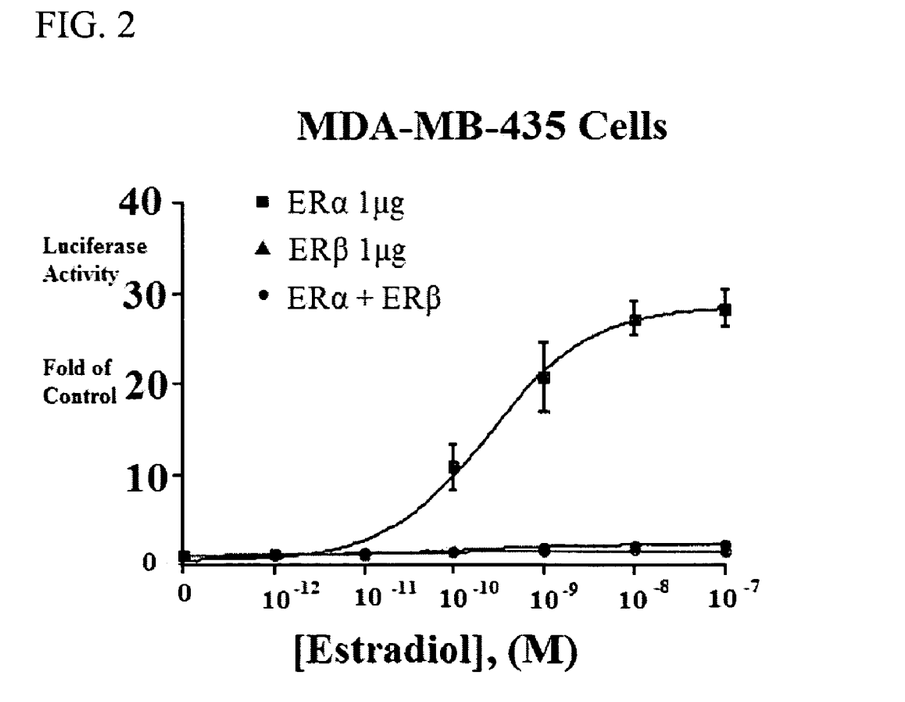
FIG. 2 is a graph of luciferase expression in MDA-MB-435 (human metastatic breast cancer) cells transformed with DNA encoding estrogen response element linked to the minimal thymidine kinase (tk) promoter and a sequence encoding luciferase (Luc) in response to varying concentrations of estradiol ($E_2$) in the presence of either estrogen receptor alpha (ERα), estrogen receptor beta (ERβ) or both. ERβ has much less stimulatory effect on the ERE than does ERα in the presence of $E_2$. Remarkably, when ERα and ERβ are coexpressed in this cell line, ERβ expression greatly reduces the ERE stimulatory effect of ERα in the presence of $E_2$.

ERβ inhibits ERα-mediated transcriptional activation of ERE-tk-Luc: Surprisingly, when ERα or ERβ were coexpressed in U937 cells, the activation by ERα is markedly inhibited (FIG. 1). These data show that ERβ exerts a repressive effect on ERα activation of ERE-tk-Luc. Similar results were observed in the breast cancer cell line, MDA-MB435 (FIG. 2). Other investigators have found a similar repressive effect of ERβ on ERα transactivation in different cell types. These studies indicate that the different activation of ERα and ERβ on ERE-tk-Luc and the repressive effect of ERβ on ERα-mediated-transcription are not cell-type specific and results from intrinsic properties of the ERs. The repression of ERα by ERβ requires the formation of an ERα/ERβ heterodimer, because mutations in helix 11 of ERβ that prevent dimerization inhibit its repression activity (data not shown).

Example 4

Materials and Methods: Reagents. Phenol red-free Dulbecco's modified Eagle's/F-12 Coon's modification medium was obtained from Sigma. Biobrene was purchased from Applied Biosystems. The U937 cell line was obtained from American Type Culture Collection. Human recombinant TNF-α was obtained from R & D Systems.

Plasmid Construction. A PstI to AhaII. fragment (−1044 to +93) from the human TNF-α gene, pLT, was cloned upstream of the luciferase cDNA. The 5' deletions were constructed by using unique restriction sites, ApaI for the −125 deletion, and StyI for the −82 deletion. Three copies of the human TNF-α promoter fragment from −125 to −82 [TNF-responsive element (TNF-RE)] or one copy of the ERE from the frog vitellogenin A2 gene (vitA2-ERE, 5'-TCAGGTCACAGTGAC-CTGA-3') (SEQ ID NO: 1) were ligated upstream of −32 to +45 herpes simplex thymidine kinase (TK) promoter linked to luciferase (TNF-RE-tk-Luc, and ERE-tk-Luc, respectively). ERβ mutants were created with QuikChange site-directed mutagenesis kits (Stratagene), by using oligonucleotides containing the mutation. The mutants were sequenced with Sequenase kits (Amersham Pharmacia) to verify the presence of the mutation.

Cell Culture, Transfection, and Luciferase Assays—U937 (human monocyte), U2OS (human osteosarcoma), MDA-MB-435 (human metastatic breast cancer), and MCF-7 (human breast cancer) cells were obtained from the cell culture facility at the University of California, San Francisco. U937 cells were maintained as described previously, whereas U2OS, MDA-MB435, and MCF-7 cells were maintained and subcultured in phenol red-free Dulbecco's modified Eagle's medium/F-12 media containing 5% fetal bovine serum, 2 mM glutamine, 50 units/ml penicillin, and 50 μg/ml streptomycin. For experiments, cells were collected, transferred to a cuvette, and then electroporated with a Bio-Rad gene pulser as described previously using 3 μg of reporter plasmid and 1 μg of ERα or ERβ expression vectors. After electroporation, the cells were re-suspended in media and plated at 1 ml/dish in 12-well multiplates. The cells were treated with $E_2$, genistein, daidzein, or biochanin A (Sigma-Aldrich) 3 h prior to exposure to 5 ng/ml TNF-α (R & D Systems) for 24 h at 37° C. Cells were solubilized with 200 μl of 1× lysis buffer, and luciferase activity was determined using a commercially available kit (Promega). The concentration of hormone required to produce a half-maximal induction ($EC_{50}$) or inhibition ($IC_{50}$) of luciferase activity was calculated with the Prism curve-fitting program (Graph Pad Software, version 2.0b). For proliferation studies, parental MCF-7 cells were subcloned at 1 cell/well in the presence of 0.1 nM $E_2$, and the fastest growing clone was selected for experiments. These cells expressed exclusively ERα as determined by reverse transcription polymerase chain reaction (RT-PCR). The cells were plated in duplicate at a density of 25,000 cells/35-mm plate in tissue culture medium containing 3% stripped fetal bovine serum. One day after plating they were treated with increasing concentrations of $E_2$ or genistein. The medium was changed every other day, and E2 or genistein was added to the medium. After 8 days the cells were counted with a Coulter counter. All experiments presented in the figures were performed at least three times, and the data were similar between experiments.

Preparation of *Morus alba* L: Samples of *Morus alba* L were ground to fine powder using a commercial electric herb grinder; 5 grams were weighed and extracted in a) 50 ml of 100% EtOH or b) 50 ml of distilled $H_2O$ was simmered at 75° Celsius for 45 minutes. The extracts (a and b) were than decanted and only the soluble material was used.

Results: Selective estrogen receptor modulating activity in U2OS Bone cells was measured using luciferase assays. U20S osteosarcoma cells were co-transfected with a classic ERE upstream of a minimal thymidine kinase (tk) promoter (ERE-tk-Luc) and expression vectors for human ERα or ERβ. *Morus alba* L. activation of ERE-tk-Luc with ERβ, and ERα ERβ produced a 4.67-fold activation of ERE-tk-Luc with 1 μl/ml *Morus alba* L. and a 4.03-fold activation of ERE-tk-Luc with 1 μl/ml on ERα. These results indicate that *Morus alba* L. activates ERE-tk-Luc by directly interacting with ERβ.

To investigate the effects of *Morus alba* L. on transcriptional repression, the −125 to −82 region of the TNF-α promoter (TNF-α-responsive element, (TNF-RE)) was used because this region mediates TNF-α activation and $E_2$ repression. $E_2$ produced a profound repression of TNF-α activation of the TNF-RE upstream of a minimal tk promoter (TNF-RE-tk-Luc) with either transfected ERα or ERβ in U2OS cells. $E_2$ can abolish TNF-α activity on ERβ (100% repression) but not on ERα (73.3% repression). *Morus alba* L. produced a large repression of TNF-α activation of TNF-RE in the presence of ERβ (109.6%) and ERα (102.8%). These results indicate that *Morus alba* L. represses TNF-α activation through TNF-RE-tk-Luc by directly interacting with ERβ and ERα.

In these experiments, the lowest dose of *Morus alba* L. extract that is effective for estrogenic activity is 1.2 μg. However, it is to be expected that in other cell systems this number may fluctuate.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

All references cited herein are incorporated herein in their entirety.

What is claimed is:

1. A method of eliciting an estrogenic effect in a post-menopausal female patient in need of such estrogenic effect, comprising administering to the post-menopausal female patient an estrogenically effective amount of a pharmaceutical composition comprising an extract from the leaves of *Morus alba* L, wherein the estrogenic effect includes treating at least one climacteric symptom.

2. The method of claim 1, wherein the extract is either an aqueous or ethanolic extract.

3. The method of claim 1, wherein the extract is an ethanolic extract.

4. The method of claim 1, wherein the at least one climacteric symptom is selected from the group consisting of hot flashes, insomnia, vaginal dryness, decreased libido, and urinary incontinence.

5. The method of claim 4, wherein the estrogenic effect includes treating hot flashes.

* * * * *